(12) United States Patent
Crompvoets et al.

(10) Patent No.: US 8,880,156 B2
(45) Date of Patent: Nov. 4, 2014

(54) METHOD AND SYSTEM FOR DETERMINING A PHYSIOLOGICAL CONDITION USING A TWO-DIMENSIONAL REPRESENTATION OF R-R INTERVALS

(75) Inventors: Floris Maria Hermansz Crompvoets, Eindhoven (NL); Martin Ouwerkerk, Eindhoven (NL); Henk Albert Hessel, Eindhoven (NL); Martijn Krans, Eindhoven (NL); Joanne Henriette Desiree Monique Westerink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1036 days.

(21) Appl. No.: 12/990,977

(22) PCT Filed: Apr. 24, 2009

(86) PCT No.: PCT/IB2009/051688
§ 371 (c)(1),
(2), (4) Date: Nov. 4, 2010

(87) PCT Pub. No.: WO2009/136306
PCT Pub. Date: Nov. 12, 2009

(65) Prior Publication Data
US 2011/0060235 A1    Mar. 10, 2011

(30) Foreign Application Priority Data

May 8, 2008    (EP) .................................... 08155890

(51) Int. Cl.
*A61B 5/04*      (2006.01)
*A61B 5/16*      (2006.01)
*A61B 5/024*     (2006.01)
*A61B 5/00*      (2006.01)
*A61B 5/0456*    (2006.01)

(52) U.S. Cl.
CPC ................ *A61B 5/02438* (2013.01); *A61B 5/16* (2013.01); *A61B 5/0456* (2013.01); *A61B 5/02405* (2013.01); *A61B 5/486* (2013.01)
USPC ......................................................... 600/509

(58) Field of Classification Search
CPC .. A61B 5/0452; A61B 5/0456; A61B 5/0006; A61B 5/7264; A61B 5/726; A61B 5/7253; A61B 5/7257
USPC .................. 600/512, 521, 300, 508–509, 513, 600/515–516, 518–519, 523; 607/5, 17–18
See application file for complete search history.

(56) References Cited

U.S. PATENT DOCUMENTS 5,565,840 A    10/1996    Thorner et al.
5,682,901 A    11/1997    Kamen (Continued)

FOREIGN PATENT DOCUMENTS

EP    1509042 A1    2/2005
EP    1753211 A2    2/2007

(Continued)

OTHER PUBLICATIONS

Guzik et al: "Correlations Between the Poincare Plot and Conventional Heart Rate Variability Parameters Assessed During Paced Breathing"; J. Physiol. Sci., Feb. 2007, vol. 57, No. 1, pp. 63-71.

(Continued)

*Primary Examiner* — Carl H Layno
*Assistant Examiner* — Jessica Anthony

(57) ABSTRACT

The physiological condition of a person is determined in physiological condition determining system by using a sensor for sampling a plurality of heart beats of the person, and using a control unit to perform the acts of: extracting a series of cardiac R-R intervals from the heart beat samples, providing a two-dimensional representation of subsequent R-R intervals, wherein two subsequent R-R interval forms an entry in the two-dimensional representation resulting in a plurality of entries, determining a centroid, an average radius and an average rotation frequency for the plurality of entries in the two-dimensional representation, determining a plurality of distances between the radius and each of the entries in the two-dimensional representation, and determining the physiological condition of the person using the radius in combination with the plurality of distances.

11 Claims, 2 Drawing Sheets

(56) References Cited

U.S. PATENT DOCUMENTS

| | | | |
|---|---|---|---|
| 6,358,201 | B1 | 3/2002 | Childre et al. |
| 6,983,124 | B1 | 1/2006 | Bayley et al. |
| 2004/0002305 | A1 | 1/2004 | Byman-Kivivuori et al. |
| 2004/0207542 | A1 | 10/2004 | Chang et al. |
| 2005/0070241 | A1 | 3/2005 | Northcutt et al. |
| 2005/0132290 | A1 | 6/2005 | Buchner et al. |
| 2005/0171447 | A1 | 8/2005 | Esperer |
| 2005/0181827 | A1 | 8/2005 | Nieminen-Sundell et al. |
| 2006/0221935 | A1 | 10/2006 | Wong et al. |
| 2007/0063849 | A1 | 3/2007 | Rosella et al. |
| 2007/0126927 | A1 | 6/2007 | Yun et al. |
| 2007/0150916 | A1 | 6/2007 | Begole et al. |
| 2007/0277092 | A1 | 11/2007 | Basson et al. |

FOREIGN PATENT DOCUMENTS

| | | | |
|---|---|---|---|
| WO | 9720305 | A1 | 6/1997 |
| WO | 2007105132 | A1 | 9/2007 |
| WO | 2007117649 | A2 | 10/2007 |
| WO | 2007123923 | A2 | 11/2007 |
| WO | 2009112990 | A1 | 9/2009 |
| WO | 2009136340 | A1 | 11/2009 |
| WO | 2009136345 | A1 | 11/2009 |

OTHER PUBLICATIONS

Marciano et al: "Quantification of Poincare Maps for the Evaluation of Heart Rate Variability": Computers in Cardiology, Sep. 1994, pp. 577-580.

Brennan et al: "Do Existing Measures of Poincare Plot Geometry Reflect Nonlinear Features of Heart Rate Variability"; IEEE Transactions on Biomedical Engineering, Nov. 2001, vol. 48, No. 11, pp. 1342-1347.

Wang et al: "Visualization of Short-Term HRV as an Index for Mental Stress Evaluation"; ICMIT 2007: Mechatronics, MEMS, and Smart Materials, Proceedings of the SPIE, Dec. 2007, vol. 6794, pp. 67943R-1-67943R-6.

Thong, T.; "Geometric Measures of Poincare Plots for the Detection of Small Sympathovagal Shifts"; Proceedings of the 29th Annual International Conference of the IEEE Engineering in Medicine and Biology Society (EMBS). Lyon, France, Aug. 2007. pp. 4641-4644.

Tulppo et al: "Quantitative Beat-To-Beat Analysis of Heart Rate Dynamics During Exercise"; American Journal of Physiology, Jan. 1996, vol. 271, No. 1, Part 2. pp. H244-H252.

Brennan et al: "Poincare Plot Interpretation Using a Physiological Model of HRV Based on a Network of Oscillators"; American Journal of Physiology-Heart and Circulatory Physiology, 2002, vol. 283, pp. H1873-H1886.

Yang, A.: "Poincare Plots: A Mini-Review", HRV 2006, 16 Page Document.

Geldard, F.: "Some Neglected Possibilities of Communication", Science: May 1960, vol. 131, No. 3413, pp. 1583-1588.

Geldard, F.: "The Cutaneous "Rabbit": A Perceptual Illusion"; Science, Oct. 1972, vol. 178, No. 4057, pp. 178-179.

Neyem et al: "Designing Emotional Awareness Devices: What One Sees Is What One Feels"; Ingeniare.Revista Chilena De Ingenieria, 2007, vol. 15. No. 3, pp. 227-235.

Patel.: "Habitat: Awareness of Daily Routines and Rhythms Over a Distance Using Networked Furniture"; Proceedings of London Communications Symposium (LCS) Sep. 2003, 4 Page Document.

International Search Report—PCT/IB2009/051688.

METHOD AND SYSTEM FOR DETERMINING A PHYSIOLOGICAL CONDITION USING A TWO-DIMENSIONAL REPRESENTATION OF R-R INTERVALS

FIELD OF THE INVENTION

The present invention generally relates to a method for determining a physiological condition of a person, and more specifically to an improved method for detecting emotionally related events using heart rate variability (HRV). The present invention also relates to a corresponding system making use of such a determination method.

DESCRIPTION OF THE RELATED ART

The field and the demand for relaxation related methods and systems/devices are currently increasing. Different tools have been developed to measure physical values of a persons body for determining the stress level of the person. Measurements generally include measuring involuntary functions such as heartbeat, digestion and respiration. Whenever the brain detects a change, the autonomic nervous system produces immediate physical responses, and the persons blood pressure, heart rate and skin moisture level change. Biofeedback uses electronic instruments to make a person aware of these changes and to teach how to better control them, and thus identify and measure how that persons body responses to stress.

It is well known that respiration modulates the heart rate (respiratory sinus arrhythmia, RSA), and meditation techniques such as yoga make use of this principle. The variation in heart rate or heart rate variability (HRV) is attributed to the autonomous nervous system (ANS). An increase in heart rate is attributed to the parasympathic (vagal) nervous system while a decrease in heart rate is attributed to the sympathetic nervous system. In Zen meditation the low frequency part of the spectrum of the heart rate variability is increased with respect to the high frequency part of the spectrum. This is regarded as beneficial (relaxing) for the well-being of the meditator.

A method using the heart rate variability for determining the physiological condition for a person is disclosed in U.S. Pat. No. 6,358,201. The method uses a frequency based analysis of the heart rate variability and generates a measure for the so-called coherence, meaning that the person being measured is breathing in a coherent way and is getting relaxed. The telltale sign for coherence is a single peak in the frequency spectrum of the heart rate variability.

There is however at least one problem with the disclosed method. This problem is due to the fact that it is based on a frequency analysis of the heart rate variability, which thereby will average a large plurality of sampled heart beats, generally in the order of 60 seconds. A system implementing the method will thus have a long "learning time" to get the first reliable coherence value after the person has come into a state of relaxation. It will additionally be very difficult to immediately detect outliers (i.e. anomalous heart beats) as a change from the coherent frequency peak only will result in a very small broadening of frequency peak. Such a system will thus be unreliable to short changes in the coherence of the person.

OBJECT OF THE INVENTION

There is therefore a need for an improved method for a determining a physiological condition of a person, and more specifically that overcome or at least alleviates the prior art reliability problems due to the use of frequency analysis of the heart rate variability.

SUMMARY OF THE INVENTION

According to an aspect of the invention, the above object is met by a method for determining a physiological condition of a person, comprising sampling a plurality of heart beats of the person, extracting a series of cardiac R-R intervals from the heart beat samples, and providing a two-dimensional representation of subsequent R-R intervals, wherein two subsequent R-R intervals forms an entry in the two-dimensional representation, wherein the method further comprises the steps of determining a centroid for the plurality of entries in the two-dimensional representation, fitting a closed curve through the plurality of entries in the two-dimensional representation, wherein the center of said closed curve coincides with said centroid, determining the distances between the closed curve and the entries in the two-dimensional representation, and determining the physiological condition of the person by determining if the determined distances are above or below a predetermined first threshold.

The general concept of the present invention is based on the fact that it is possible to determine a physiological condition, such as the coherence, of a person by performing a time based analysis of the heart rate variability, i.e. of a plurality of cardiac R-R intervals (i.e. the time elapsing between two consecutive R waves, also denoted as "interbeat interval", IBI) extracted from a plurality of heart beat samples. Modeling of subsequent R-R intervals as a delay map, for example essentially as a Poincaré model (i.e. the n:th measured R-R interval is plotted on the x-axis versus the n+i:th measured R-R interval on the y-axis), generally results in an elliptic representation of the entries. However, by means of the novel concept of the invention which includes the determination of the centroid of the "cloud" of entries, the determination of the radius of the cloud of entries, after which the distance to each of the entries are related to the radius of the cloud, the physiological condition of the person can be determined. It should however be noted that a proper ellipse forming the contour of the two-dimensional representation of the entries (or circle after resealing) is generally only measured when the person is breathing coherently.

In case the distance between each of the entries and the radius is small, i.e. the thickness of the line of the ellipse is small, then this is a measure for the coherence of the person. That is, when the person is coherent the heart rate variability (HRV) and the breathing period for the person are strongly correlated, almost one to one almost: breathing period=HRV period. Thus, the present invention solves the problem of determining a coherent state of the person without having to reside to a frequency analysis of the heart rate variability of the person. That is, the more homogeneous the entries of two-dimensional representation are arranged, the more coherent is the person being measured. An advantage with the present invention following from this solution is thus that the time it takes for determining the coherent state of the person is minimized at the same time as it is possible to quickly detect a change in the state as each of the entries are directly related to the radius of the ellipse. Additionally, as each entry is analyzed individually due to the time based analysis (in comparison to the averaging used in the frequency based analysis used in prior art) it is possible to in real time individually analyze the location of each new entry with respect to each of the prior entries. It should be noted that a physically young and fit person generally will have a larger radius, whereas an older physically ill person will have a smaller radius. It should be noted that the method may include determining r and φ for the plurality of entries in the two-dimensional representation.

In a preferred embodiment of the present invention, the step of determining includes the step of determining the variance between of the plurality of entries in the two-dimensional representation in relation to the determined radius. Accordingly, it is thus possible to easily determine a relation between the different entries and the variance and/or radius of the elliptic representation, also including the possibility to determining if the distance and/or variance is above or below a predetermined first threshold, which thereby could raise an alarm to the person. The alarm can for example include at least one of an audio stimulus, visual stimulus, haptic stimulus, and such stimuli can also be used for guiding the person such that the distance/variance is minimized. Similarly, the variance may include the determination of both radius dr and rotation frequency dφ based on the determined r and φ for the plurality of entries. This concept is further elaborated below.

Furthermore, for limiting the processing power needed for executing the method according to the present invention, the step of providing a two-dimensional representation of subsequent R-R intervals comprises the step of transforming the two-dimensional representation of entries to coincide with a circle, i.e. a transformation from an ellipse to a circle. Further discussing relating to the circle transformation are made in the detailed description of the present invention.

In an alternative embodiment of the invention, the physiological condition is determined for a plurality of persons for measuring at least one of indifference, true attention and anger of the persons during a time of decision taking. Such an embodiment may for example be used for acceptance monitoring of a group of persons, for monitoring the emotional reaction to ideas and (political) proposals presented to the public, and thus obtain objective measurements on the emotional impact of the proposed ideas. Additional possibilities include trends analysis of certain proposals. Accordingly, new proposals might evoke strong emotional reactions the first time they are presented, either in positive or in negative sense. However, after one has become more familiar with the proposal, these strong first reactions might wear out (not always, but sometimes), and maybe a more balanced view surfaces. That is, collective parameters, such as coherent responses provide information on which factions in the group show similar attitudes. The gathered information can be used either by the group or by a process facilitator to guide the decision taking process. For additionally increasing the reliability of such measurements, it is possible to include the determination of the galvanic skin response for the plurality of persons, and use the resulting response in measuring the indifference, the true attention and the anger.

In an embodiment of the invention, at least one of the persons are located remotely from the reminder of the persons, and the measurement results from that person's sensor for sampling a plurality of heart beats and/or means for determining the galvanic skin response are transmitted to the control unit over a network such as the Internet. Such an implementation thus provides for the possibility to use the inventive system in relation to a web based idea presentation, TV, and/or other different electronic mass communication.

Additionally, the method according to the invention may be implemented as a computer program (computer software) running on for example a microprocessor (e.g. general purpose computer) or a similar device such as a set-top box, part of a television set (built-in), a DVD player, or a portable device.

According to a further aspect of the invention, there is provided a system for determining a physiological condition of a person, comprising at least one sensor for sampling a plurality of heart beats of the person, and a control unit adapted for extracting a series of cardiac R-R intervals from the heart beat samples, and providing a two-dimensional representation of subsequent R-R intervals, wherein two subsequent R-R interval forms an entry in the two-dimensional representation, wherein the control unit is further adapted for determining a centroid and a radius for the plurality of entries in the two-dimensional representation, determining a plurality of distances between the radius and each of the entries in the two-dimensional representation, and determining the physiological condition of the person using the radius in combination with the plurality of distances.

As described above in relation to the method according to the present invention, this novel system provides a plurality of advantages over prior art due to the fact it solves the averaging and reliability problem in prior art that are due to the frequency analysis of the heart rate variability.

In a preferred embodiment of the present invention, the at least one sensor for sampling a plurality of heart beats is at least one of a photoplethysmograph, an ECG recorder, or a device for measuring a ballistocardiogram. The skilled addressee however understands that different sensors can be used and that the above examples are non-limiting.

BRIEF DESCRIPTION OF THE DRAWINGS

These and other aspects of the present invention will now be described in more detail, with reference to the appended drawings showing currently preferred embodiments of the invention, in which.

DETAILED DESCRIPTION OF CURRENTLY PREFERRED EMBODIMENTS

Figure 1:
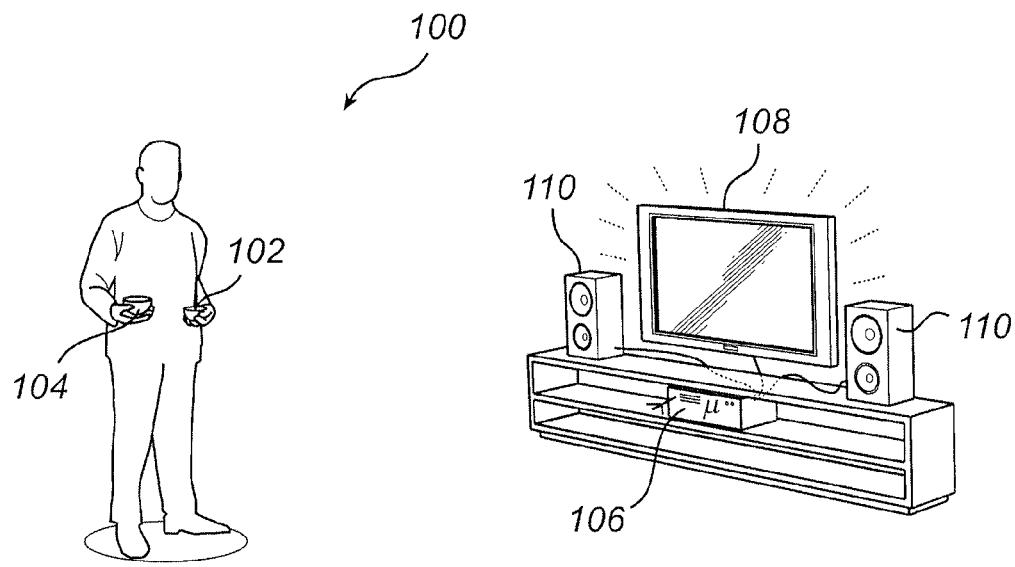
FIG. 1 is a block diagram illustrating a system according to an embodiment of the present invention.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Figure 2:
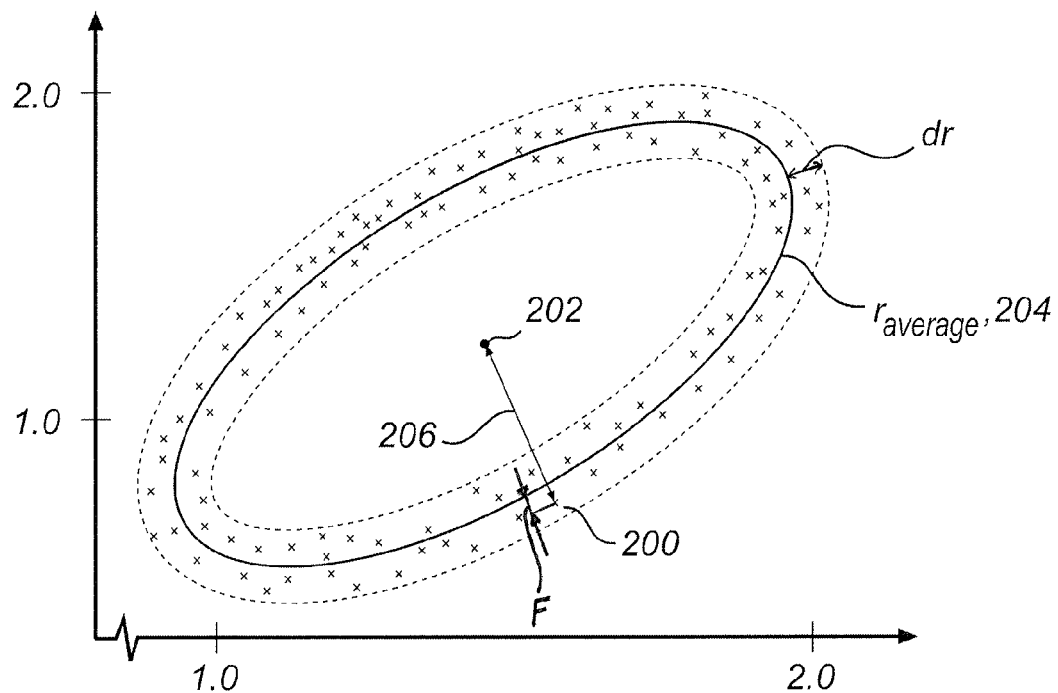
FIG. 2 is a graph illustrating a two-dimensional representation of subsequent R-R intervals (labels on the two axes: x-axis IBI time n, y-axis IBI time n+1)

Referring now to the drawings and to FIGS. 1 and 2 in particular, there are depicted a block diagram of a system 100 according to an embodiment of the present invention, and a two-dimensional graphical representation of subsequent R-R intervals determined by the system 100, respectively. FIGS. 1 and 2 will be discussed simultaneously. The system 100 measures, compares and gives feedback on the HRV signals acquired by the system 100 via sensors 102 and 104. Each sensor 102 and 104 measures the heart beat of a person, i.e. are arranged such that they can detect the heart beat of the person. An advantage of using multiple sensors is that it is possible to combine the data of the different sensors and improve reliability, e.g. reducing motion artifacts. The skilled addressee however understands that more than or less than two sensors are possible and thus possible within the scope of the invention. Examples of sensors that can detect heart beat are a photoplethysmograph, an ECG recorder, or a device for measuring a ballistocardiogram (e.g. Emfit sensor, MyHeart project).

The system 100 additionally comprises a control unit 106 which receives the heart beat samples from the sensors 102 and 104, such as a microprocessor or the like, for extracting a series of cardiac R-R intervals (or "interbeat interval", IBI) from the heart beat samples, i.e. the heart rate variability (HRV) of the person, and for providing a two-dimensional representation of subsequent R-R intervals, wherein two subsequent R-R interval forms an entry 200 in the two-dimensional representation. The control unit 106 preferably comprises wireless capabilities for the reception of the heart beat measurements. The connection can however of course be provided by means of wire. As discussed above, the two-dimensional representation is preferably essentially a Poincaré model of subsequent R-R intervals, i.e. the n:th measured IBI is plotted on the x-axis versus the n+i:th measured IBI on the y-axis. Additionally, the control unit 106 is preferably further adapted to determining a centroid 202 and an average radius 204 for the plurality of entries in the two-dimensional representation, i.e. the center of the entries represented as a two-dimensional plot where the essentially the contour (i.e. the closed curve fitted through the entries of the two-dimensional representation) has the form of an ellipse and from which the centroid to the ellipse essentially represents the radius 204. That is, one average radius may generally only be determined after conversion from ellipse to circle. However, it is possible to define a kind of average ellipse but that is more complicated as it is necessary to determine the averages of the two axes of the ellipse. Also, the control unit 106 is adapted to determine a distance 206 between the centroid 202 and each of the entries in the two-dimensional representation, wherein the distance for each of the entries thus individually can be analyzed and compared with the average radius 204 for the entries. The result of the analysis, which also is performed by the control unit 106, can then be used for determining the physiological condition of the person.

The system 100 can also provide stimulus and feedback possibilities, wherein the stimulus for example may include the rendering of an audio-visual (e.g. audio and/or video) experience by means of a TV set 108 and speakers 110 specifically adapted for providing such stimulus, including a breathing pacer stimulus shown to the person. Also, in case of a TV set 108 comprising ambilight (or similar), the ambilight lighting concept can be used for further enhancing the audio-visual experience. Other additional arrangements are of course possible, including for example haptic stimulation of the person, using different types of actuators arranged in the close vicinity of the person, for example embedded into a textile garment being worn by the person or a sofa/chair having embedded actuators. However, the TV set need not necessary have to be specifically adapted, and for example a set-top box or DVD player may instead be adapted for providing the above mentioned stimulus, including a specifically adapted DVD disc for the DVD player (or similar portable or fixed storage device) having stored thereon an information pattern for providing stimulation and guidance for the person such that the person quickly can reach a state of coherence (e.g. quickly de-stress).

The TV set 108 and/or the above mentioned DVD player may for example be adapted in accordance to the concept of Relax TV which provides a slow down experience that allows a person to easily relax in the comfort of their home. The person using the system 100 can just lean back in the sofa, hold a sensor 102, 104 in each hand, breathe in pace with a movie clip displayed on the TV set 108, and witness his or her relaxation level rise by means of for example a graphical feedback interface displayed on the TV set 108. After a few minutes the user achieves a relaxed state by following a tailored breathing rhythm exercise which is visualized on the TV set 108, comprising special audiovisual content and/or ambilight (as discussed above) with account taken to the heart rhythm and relaxation performance of the user. An example the Relax TV concept is disclosed in the European patent application no. 08152732.7 (applicant's reference PH009672) which is completely incorporated by reference.

However, it should be noted that the slow down experience is not limited to the TV 108 only, but may be provided by other rendering devices as well. For instance, a biofeedback relaxation experience can be integrated in a lighting system or music player. Alternatively, it could be used to facilitate the process of falling asleep by integrating it into an alarm clock or Wake-up Light.

As is clear from FIG. 2 the entries in the two-dimensional representation are by default arranged in an elliptic shape, and for i=0 the plot will be a straight line through the origin. However, for determining the radius and the distances, and for making use of those determination in the analysis, extensive computation is necessary. Thus, it is desirable to perform a circular transformation (i.e. ellipse to circle) as it takes less calculation power to analyze a circle then an ellipse. To do this the data on both axes are shifted 90 degrees with respect to each other.

In order to get a circular plot it is necessary to plot IBI n vs. IBI n+$i_{circle}$. Here, $i_{circle}$ is estimated in the following way:

$$i_{circle} = \left[\frac{T_{pacer}}{IBI_{average}}\right] \bigg/ 4$$

where $T_{pacer}$ is the period of the pacer in seconds and $IBI_{average}$ is the average IBI in seconds. The ratio $T_{pacer}/IBI_{average}$ is the number of datapoints for one pass of the ellipse. Dividing this number by 4 as shown in the equation above gives the 90 degrees phase factor to turn the ellipse into a circle.

The feedback to the user is in this case the ellipse (circle). In other words, an opener and thinner ellipse represents a more "coherent state", i.e. good syncing between breathing pace and heart rate. The radius of the ellipse (i.e. size) is a measure for the amplitude of the heart rate variability (HRV), and the thickness of the line of the ellipse, i.e. the variation in radius, is a measure for the coherence. A discussed above, when the person is coherent the HRV and the breathing period are strongly correlated, almost one to one almost: breathing period=HRV period.

Breaks of the coherence state, as the result of getting distracted or startled, result in abrupt and immediate deviation from the ellipsoidal path. This allows fast detection of an event and also fast visualization. If as determined above the radius 204 of the circle has a certain distribution with an average radius $r_{average}$, and a width dr it is possible to set a measure for when a point is an abrupt deviation from the circular path.

Figure 3:
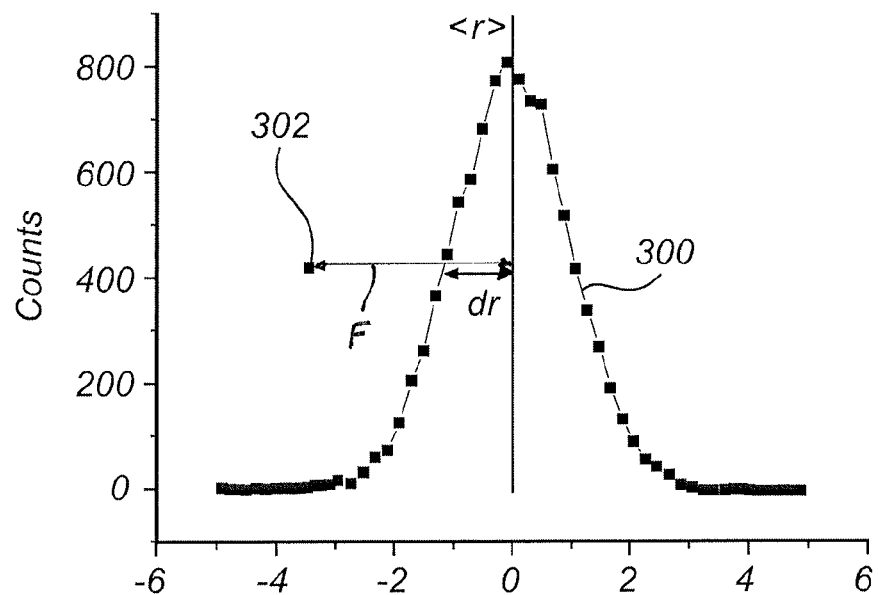
FIG. 3 is a histogram plot of radii distribution.

When a measured radius (i.e. a distance d between the centroid 202 and the specific entry 200) deviates significantly from the average radius raverage then this point is labeled as an event and it is not taken into account for the distribution (dr and raverage). This is a filtering method; however other suitable filtering or data point rejections schemes can be used as well. Of course, initially it is necessary to builds a proper distribution with sufficient data points. However, the larger the number of data points the better the distribution becomes and the better the event detection works. In other words, a longer history is built up. An example of a histogram plot 300 of distribution is shown in FIG. 3. In this example, when the distance 206, d, of a measured data point deviates more than 3 times dr from the average radius raverage: F=|d−raverage|>3dr, then this point is labeled as an event 302. Here, F denotes the difference (also called "distance" hereinafter) between the distance d of an entry and the closed curve 204. The criteria for when a point deviates significantly can be set manually by the user of the system 100 or automatically by the system 100 (based on the radii distribution and statistical theory).

In comparison to prior art methods and systems that detect events (i.e. breaks of coherence) in about 10 seconds and use an analysis in the frequency domain, the ellipsoidal visualization method according to the present invention detect events in about one second (i.e. on the timescale of an IBI measurement). Fast detection is advantageous, because feedback and corrective measures, such as respiration pacing can be much faster, leading to a speedy recovery of the coherent state. Thus, the experience of the person trying to de-stress is enhanced.

However, it should furthermore been noted that the method for determining a physiological condition of a person also may be used in relation to decision taking by a group of persons. As such, the psychophysiological response to propositions may be monitored for all persons in the group, and individual parameters, such as indifference, true attention and anger can be discriminated by interpretation of heart rate variability (HRV) and/or galvanic skin response can be determined. Collective parameters, such as coherent responses provide information on which factions in the group show similar attitudes. However, it should be noted that the psychophysiological response of the persons in the group can be done with or without the inclusion of the specific HRV method discussed above.

Figure 4:
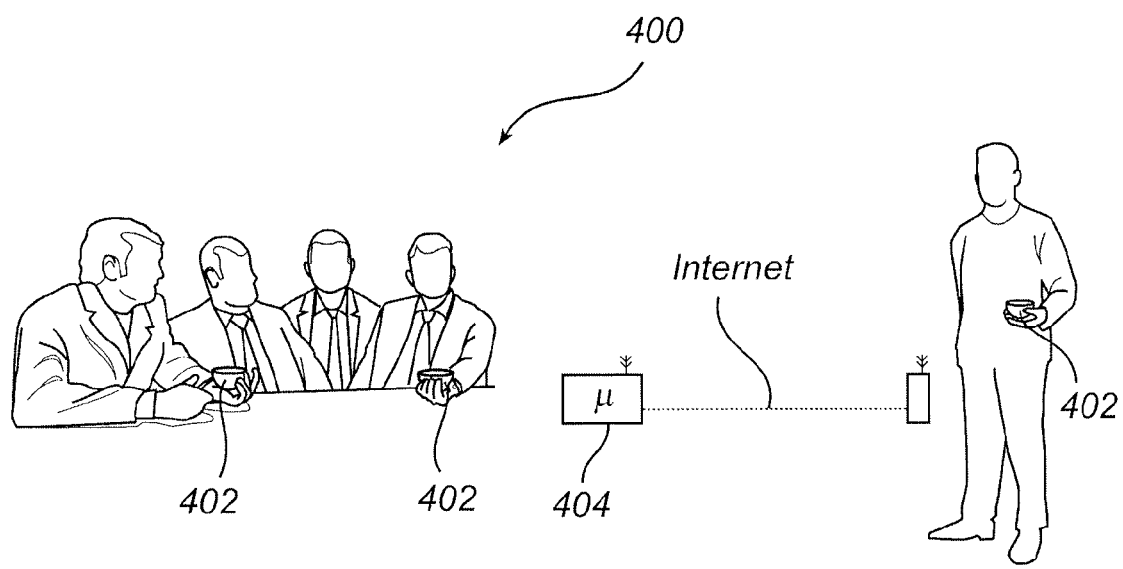
FIG. 4 is a conceptual set-up of a decision taking system using the method according to the present invention.

In FIG. 4, an example of a decision taking system 400 is illustrated. Each of the persons in the group, for example in relation to a meeting, are provided with at least one sensor for measuring the heart beat and/or the skin conductance. In the illustrated embodiment, the sensor arrangement (i.e. both heart beat and skin conductance) are integrated into a single sensor device 402, further comprising wireless capability for communicating with a central control unit 404. In the embodiment, an additional person/participant is arranged remotely from the remainder of the persons, for example by means of teleconference or video conferencing. In this case, also that person has been equipped with a sensor device 402 which is connected to the control unit 404 by means of a network connection, such as the Internet.

During the analysis of the individual persons it is essential that time synchronization between voting and measurements are correct. Thus, the system 400 records a timestamp for each measurement. Accordingly, if a distance D between the level of acceptance of a person and the official outcome of the decision is defined, then this distance will be a function of the overall outcome of the decision, the individual, personal vote, the measured physiological data at the moment the person voted and the measured physiological data at the moment the person becomes aware of the official outcome. The formula is given by $$D=f(\text{vote}_{person}-\text{outcome}_{total})+g(\text{measdata}_{after}-\text{measdata}_{voting})$$

Here, a sub-function, $f$, is defined to determines how far the person's vote, $\text{vote}_{person}$, differs from the total outcome $\text{outcome}_{total}$ and a sub-function, g to determines how far the measured data at official outcome, $\text{measdata}_{after}$, differs from the measured data during voting $\text{measdata}_{voting}$.

The distance function D can then be regarded as a kind of weighting factor. The larger the distance the more the person disagrees with the official outcome. To get a reliability measure we can discern the following four situations as shown in the table below.

| Outcome of functions (f + g) | Distance (D) | Level of agreement |
|---|---|---|
| f small + g small | small | Strongly agrees |
| f large + g small | medium | Doubts |
| f small + g large | medium | Doubts |
| f large + g large | large | Strongly disagrees |

When synchronization is done as mentioned above with time stamps people both at a remote location and locally present can be evaluated simultaneously. The latency between response detection and feedback needs to be short enough to create the perception of real-time monitoring. The heart rate variability analysis algorithm as described above for attention lapses and shifts can be used to analyze the data. Utilization of such an algorithm in the setting of a meeting where a proposal is presented allows indifference to be discriminated from interest for the participants. In the above described manner individual parameters, such as indifference, true attention and anger can be discriminated by interpretation of heart rate variability and galvanic skin response. Collective parameters, such as coherent responses provide information on which factions in the group show similar attitudes. The gathered information can be used either by the group or by a process facilitator to guide the decision taking process. The above described system 400 is especially useful in relation to acceptance monitoring for decision taking, as a feedback tool for the decision taking process, in conjunction with e-voting (e.g. tele-voting).

The skilled addressee realizes that the present invention by no means is limited to the preferred embodiments described above. On the contrary, many modifications and variations are possible within the scope of the appended claims. For example, the decision taking system as discussed above can be used with other types of methods for determining the physiological condition of a person, such as for example one of the prior art HRV monitoring methods using frequency analysis.

Furthermore, in performing the circle transformation, it is possible to initially determine the centre of mass (i.e. centroid) of the entries in the two-dimensional representation, after which the angle ($\phi$) with respect to a horizontal axis and the distance (r) with respect to the centre of mass coordinate is determined for each entry which yields a new coordinate (r, $\phi$). The angle is plotted as a function of time, and a linear fit is made to this curve. The first derivation yields the rotation frequency f. From this the period T=1/f is determined, and this period is equivalent to $T_{pacer}/IBI_{average}$. The time shift to transform the ellipse into a circle is then given by $\Delta t=T/4$. Similarly, deviations dr in the distance r or the deviations d$\phi$ in the angle $\phi$ can be used as a measure for the coherence. In the latter case the deviations d$\phi$ are compared to the average rotation frequency f. For the deviation in r it is possible to use a similar measure as described above (dr/r).

The invention claimed is:

1. A method for determining a physiological condition of a person, the method operating in a physiological condition determining system, the method comprising:
    using a sensor of the physiological condition determining system for sampling a plurality of heart beats of the person;
    extracting in a control unit of the physiological condition determining system a series of cardiac R-R intervals from the heart beat samples; and
    using the control unit for providing a two-dimensional representation of subsequent R-R intervals, wherein two subsequent R-R intervals form an entry in the two-dimensional representation resulting in a plurality of entries in the two-dimensional representation,
    determining in the control unit a centroid, for the plurality of entries in the two-dimensional representation;
    fitting in the control unit a closed curve through the plurality of entries in the two-dimensional representation, wherein a center of said closed curve coincides with said centroid
    determining in the control unit distances between the closed curve and the plurality of entries in the two-dimensional representation; and
    determining in the control unit the physiological condition of the person by determining if the determined distances are above or below a predetermined first threshold.

2. The method of claim 1, comprising determining in the control unit a variance between the entries in the two-dimensional representation in relation to a determined average radius of the closed curve.

3. The method of claim 1, wherein the two-dimensional representation of entries is essentially a Poincaré model of subsequent R-R intervals.

4. The method of claim 1, wherein providing a two-dimensional representation of subsequent R-R intervals comprises transforming in the control unit the two-dimensional representation of entries to coincide with a circle.

5. The method of claim 1, wherein the physiological condition for the person is a measure of coherence for the person.

6. The method of claim 1, wherein fitting a closed curve through the plurality of entries in the two-dimensional representation is adapted for fitting in the control unit an ellipse through the plurality of entries.

7. The method of claim 1, comprising outputting from the control unit at least one of an audio stimulus, visual stimulus, haptic stimulus if a change in the physiological condition is above or below a predetermined second threshold.

8. The method of claim 1, comprising the step of outputting from the control unit at least one of an audio stimulus, visual stimulus, haptic stimulus for guiding the person such that the distance between a radius and an entry is minimized.

9. The method of claim 1, wherein the physiological condition is determined for a plurality of persons for measuring at least one of indifference, true attention and anger of the persons during a time of decision taking.

10. A system for determining a physiological condition of a person, the system comprising:
    at least one sensor for sampling a plurality of heart beats of the person; and
    a control unit adapted for:
        extracting a series of cardiac R-R intervals from the heart beat samples; and
        providing a two-dimensional representation of subsequent R-R intervals, wherein two subsequent R-R intervals form an entry in the two-dimensional representation resulting in a plurality of entries in the two-dimensional representation,
        determining a centroid, for the plurality of entries in the two-dimensional representation;
    fitting a closed curve through the plurality of entries in the two-dimensional representation, wherein a center of said closed curve coincides with said centroid;
        determining of a distance between the closed curve and the plurality of entries in the two-dimensional representation; and
        determining the physiological condition of the person by determining if the determined distances are above or below a predetermined first threshold.

11. A method for determining a physiological condition of a person, the method operating in a physiological condition determining system, the method comprising:
    using a sensor of the physiological condition determining system for sampling a plurality of heart beats of the person;
    extracting in a control unit of the physiological condition determining system, a series of cardiac R-R intervals from the heart beat samples; and
    providing in the control unit a two-dimensional representation of subsequent R-R intervals, wherein two subsequent R-R intervals form an entry in the two-dimensional representation resulting in a plurality of entries in the two-dimensional representation,
    determining in the control unit a centroid, an average radius and an average rotation frequency for the plurality of entries in the two-dimensional representation;
    determining in the control unit a plurality of distances between a radius and each of the plurality of entries in the two-dimensional representation; and
    determining in the control unit the physiological condition of the person by using the radius in combination with the plurality of distances.

* * * * *